(12) United States Patent
Ma et al.

(10) Patent No.: US 11,992,469 B2
(45) Date of Patent: May 28, 2024

(54) TARGETING MITOCHONDRIAL DYNAMICS BY MITOCHONDRIAL FUSION PROMOTER M1 AS A TREATMENT STRATEGY FOR NERVOUS SYSTEM INJURY

(71) Applicant: City University of Hong Kong, Hong Kong (CN)

(72) Inventors: Chi Him Eddie Ma, Hong Kong (CN); Ngan Pan Bennett Au, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 21 days.

(21) Appl. No.: 17/448,215

(22) Filed: Sep. 21, 2021

(65) Prior Publication Data

US 2022/0087957 A1    Mar. 24, 2022

Related U.S. Application Data

(60) Provisional application No. 63/081,371, filed on Sep. 22, 2020.

(51) Int. Cl.
*A61K 31/15* (2006.01)
*A61P 25/02* (2006.01)

(52) U.S. Cl.
CPC .............. *A61K 31/15* (2013.01); *A61P 25/02* (2018.01)

(58) Field of Classification Search
CPC ................................ A61K 31/15; A61P 25/02
See application file for complete search history.

(56) References Cited

U.S. PATENT DOCUMENTS

| | | | |
|---|---|---|---|
| 10,578,610 | B2 | 3/2020 | Mochly-Rosen et al. |
| 2006/0160812 | A1* | 7/2006 | Schubert .............. C07D 231/12 |
| | | | 544/333 |

FOREIGN PATENT DOCUMENTS

| | | | | |
|---|---|---|---|---|
| JP | 2010222318 A | | 10/2010 | |
| JP | 2010222319 A | | 10/2010 | |
| WO | WO 2022/174062 | * | 8/2002 | ............. A61K 38/18 |

* cited by examiner

*Primary Examiner* — Alicia L Otton
(74) *Attorney, Agent, or Firm* — S&F/WEHRW

(57) ABSTRACT

Provided herein are methods of treating a nerve injury in a subject in need thereof and methods of treating an injured neuron using diaryl hydrazones.

19 Claims, 9 Drawing Sheets

TARGETING MITOCHONDRIAL DYNAMICS BY MITOCHONDRIAL FUSION PROMOTER M1 AS A TREATMENT STRATEGY FOR NERVOUS SYSTEM INJURY

CROSS-REFERENCE TO RELATED APPLICATIONS

This application claims priority from U.S. Provisional Patent Application No. 63/081,371, filed on Sep. 22, 2020, the content of which is hereby incorporated by reference in its entirety.

TECHNICAL FIELD

The present disclosure relates to small molecule mitochondrial fusion promoters useful in treatment of nervous system injuries and treatment of injured neurons, such as retinal ganglion cells and dorsal root ganglion neurons.

BACKGROUND

Injuries to the nervous system often result in persistent and irreversible sensory and motor function deficits in patients. Proximal peripheral nerve injuries, such as brachial plexus injuries, require long-distance axon regeneration for target muscle reinnervation and motor functional recovery. The intrinsic growth capacity of adult peripheral neurons is very limited and the rate of axonal regrowth is slow (i.e. 1-2 mm/day). Although the peripheral axons can regenerate into their target muscles, they fail to reform functional synapses at the motor endplate for motor functional recovery largely due to prolonged muscle denervation. In the central nervous system (CNS), the absence of neuronal intrinsic growth capacity and the presence of extrinsic growth inhibitors are the major obstacle for successful axon regeneration.

Currently, there are no effective drugs for treating patients with nervous system injuries. Surgery is commonly used for nerve repair resulting in limited functional recovery. In the adult mammalian central nervous system, neurons fail to regenerate their axons after injury due largely to the lack of intrinsic growth capacity. There is no effective treatment strategy available to rekindle intrinsic growth capacity of injured neurons in the market.

There thus exists a need to develop new methods of treating nervous system injuries.

SUMMARY

The present disclosure relates to the therapeutic use of a class of diaryl hydrazones, exemplified by M1, as mitochondrial fusion promoters in axon regeneration after central and peripheral nerve injuries. M1 and its analogs can markedly increase the intrinsic growth capacity of adult dorsal root ganglion neurons in vitro and accelerate axon regeneration after in vivo peripheral nerve injuries in mice. Remarkably, intravitreal injection of M1 induced robust axonal regrowth with some of the regenerating axons reaching superior colliculus and able to elicit neuronal firing six weeks after optic nerve crush injury. It is found that M1 is suitable for use in treating patients with nervous system injuries. M1 has the structure:

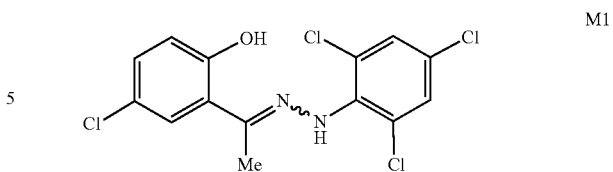

The diaryl hydrazone mitochondrial fusion promoters, exemplified by M1, were identified as potent small molecules to enhance the intrinsic growth capacity of adult neurons, and determined the therapeutic potential of mitochondrial fusion promoter M1 small molecule in accelerating nerve repair after peripheral and central nervous system injury.

In a first aspect, provided herein is a method of treating a nerve injury in a subject in need thereof, the method comprising administering a therapeutically effective amount of a compound to the subject, wherein the compound has Formula I:

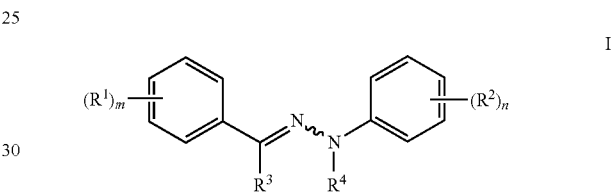

or a conjugate salt thereof, wherein m is a whole number selected from 1-4;

n is a whole number selected from 1-4;

$R^1$ and $R^2$ for each instance is independently selected from the group consisting of halide, nitrile, nitro, phosphate, alkyl, alkenyl, alkynyl, cycloalkyl, heterocycloalkyl, aryl, aralkyl, heteroaryl, —OR, —SR, and —$NR_2$;

$R^3$ is hydrogen or alkyl;

$R^4$ is hydrogen or alkyl; and

R for each instance is independently selected from the group consisting of hydrogen, alkyl, alkenyl, alkynyl, cycloalkyl, heterocycloalkyl, aryl, aralkyl, and heteroaryl.

In certain embodiments, $R^3$ is $C_1$-$C_6$ alkyl.

In certain embodiments, $R^4$ is hydrogen.

In certain embodiments, $R^1$ and $R^2$ for each instance is independently halide, nitrile, nitro, phosphate, —OR, —SR, and —$NR_2$, wherein R for each instance is independently hydrogen or alkyl.

In certain embodiments, $R^1$ and $R^2$ for each instance is independently halide or hydroxyl.

In certain embodiments, m is a whole number selected from 1-2; n is a whole number selected from 1-3; $R^1$ and $R^2$ for each instance is independently halide, nitrile, nitro, phosphate, —OR, —SR, and —$NR_2$, wherein R for each instance is independently hydrogen or alkyl; $R^3$ is $C_1$-$C_6$ alkyl; and $R^4$ is hydrogen.

In certain embodiments, the compound has the Formula II:

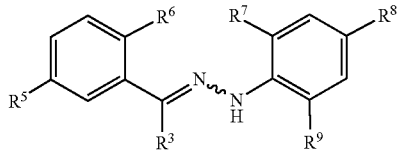

or a conjugate salt thereof, wherein each of $R^5$, $R^6$, $R^7$, $R^8$, and $R^9$ is independently halide, nitrile, nitro, phosphate, methyl, —OR, —SR, or —$NR_2$, wherein R for each instance is independently hydrogen or alkyl; and $R^3$ is $C_1$-$C_6$ alkyl.

In certain embodiments, each of $R^5$, $R^6$, $R^7$, $R^8$, and $R^9$ is independently halide, methyl, or OR, wherein R for each instance is independently hydrogen or $C_1$-$C_6$ alkyl.

In certain embodiments, $R^3$ is methyl.

In certain embodiments, the compound is:

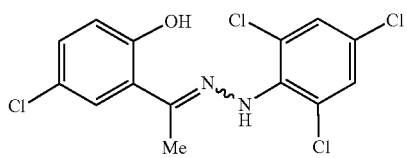

or a conjugate salt thereof.

In certain embodiments, the nerve injury comprises at least one of a central nervous system injury or a peripheral nervous system injury.

In certain embodiments, the compound promotes the regrowth of injured axons.

In certain embodiments, the compound is administered intravitreally, intraperitoneally, suprachoroidally, subconjunctivally, retrobulbarly, intracamerally, or subretinally.

In certain embodiments, the compound is co-administered with a therapeutically effective amount of a phosphatase and tensin homolog (Pten) inhibitor.

In a second aspect, provided herein is a method of treating an injured neuron, the method comprising contacting the injured neuron with a compound, wherein the compound has Formula I:

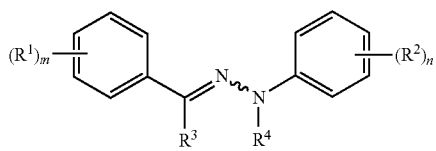

or a conjugate salt thereof, wherein
m is a whole number selected from 1-4;
n is a whole number selected from 1-4;
$R^1$ and $R^2$ for each instance is independently selected from the group consisting of halide, nitrile, nitro, phosphate, alkyl, alkenyl, alkynyl, cycloalkyl, heterocycloalkyl, aryl, aralkyl, heteroaryl, —OR, —SR, and —$NR_2$;

$R^3$ is alkyl;
$R^4$ is hydrogen or alkyl; and
R for each instance is independently selected from the group consisting of alkyl, alkenyl, alkynyl, cycloalkyl, heterocycloalkyl, aryl, aralkyl, and heteroaryl, wherein the step of contacting the injured neuron occurs in vitro or ex vivo.

In certain embodiments, m is a whole number selected from 1-2; n is a whole number selected from 1-3; $R^1$ and $R^2$ for each instance is independently halide, nitrile, nitro, phosphate, —OR, —SR, and —$NR_2$, wherein R for each instance is independently hydrogen or alkyl; $R^3$ is $C_1$-$C_6$ alkyl; and $R^4$ is hydrogen.

In certain embodiments, the compound has the Formula II:

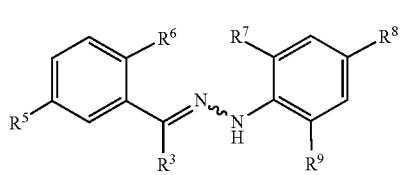

or a conjugate salt thereof, wherein each of $R^5$, $R^6$, $R^7$, $R^8$, and $R^9$ is independently halide, nitrile, nitro, phosphate, methyl, —OR, —SR, or —$NR_2$, wherein R for each instance is independently hydrogen or alkyl; and $R^3$ is $C_1$-$C_6$ alkyl.

In certain embodiments, each of $R^5$, $R^6$, $R^7$, $R^8$, and $R^9$ is independently halide, methyl, and OR, wherein R for each instance is independently hydrogen or $C_1$-$C_6$ alkyl.

In certain embodiments, the compound is:

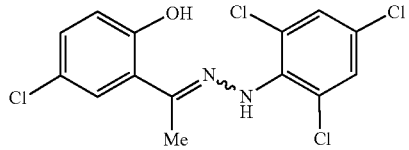

or a conjugate salt thereof.

In certain embodiments, the injured neuron is an injured retinal ganglion cell or an injured dorsal root ganglion neuron.

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Figure 1:
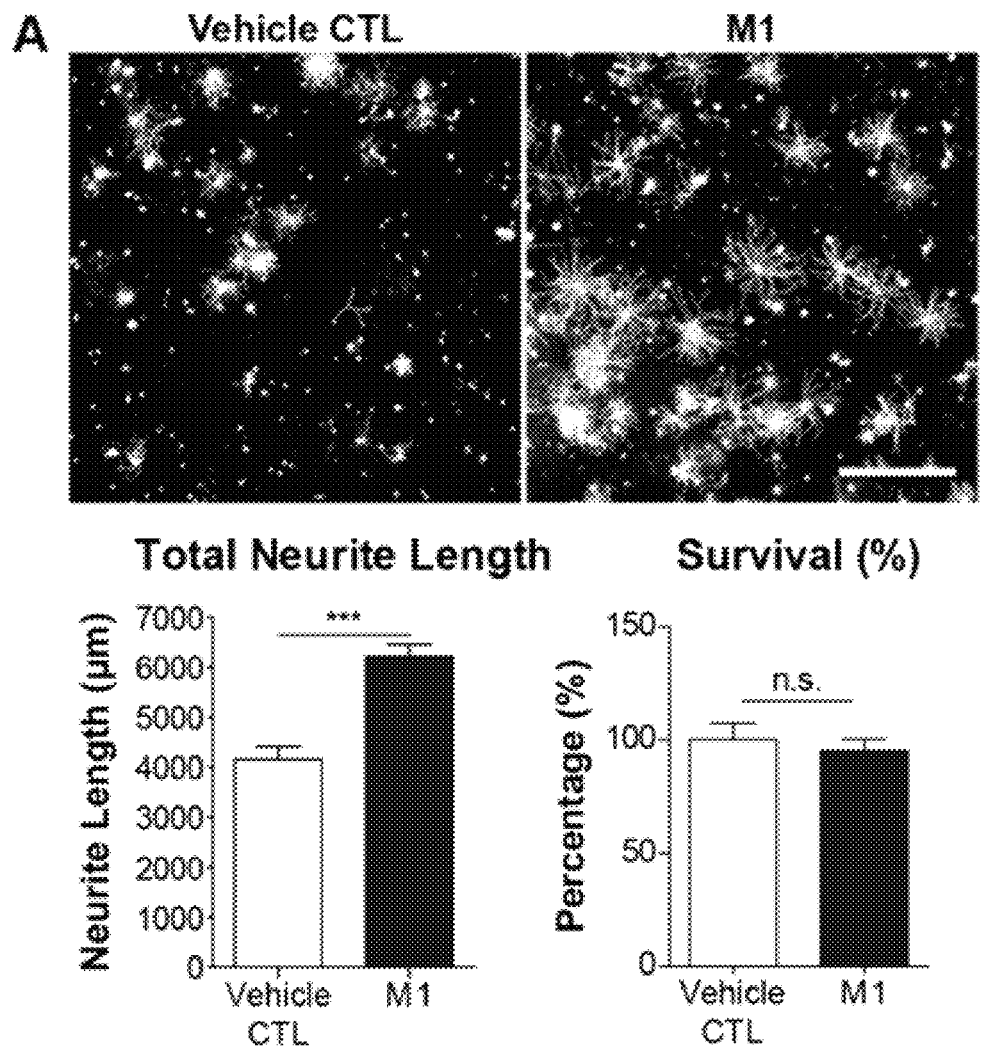
FIG. 1 depicts data showing that M1 increases the length of regenerating axons which is directly proportional to the size of mitochondria in DRG neurons. Wildtype adult DRG neurons were treated with M1 at a concentration of 2.5 μM, and 0.1% DMSO was used as vehicle controls. After 17 hours of incubation, cultures were fixed and immunostained with anti-βIII-tubulin antibodies for neurite outgrowth assay. (A) M1 treatment induced a robust neurite outgrowth from DRG neurons. Average neurite length of M1-treated DRG neurons was markedly increased compared with controls. M1 treatment did not affect cell survival of DRG neurons. Scale bar: 500 μm. (B) DRG neurons with larger mitochondria at their distal axons displayed much elongated neurites, while DRG neurons with smaller mitochondria at their distal axons displayed significantly shorter neurites. M1 treatment induced an increase in neurite extension which is associated with an increase in mitochondrial size. More than 80 DRG neurons were quantified from each treatment group. Mean±SEM of triplicates. ***P<0.001; Student's t-test. n.s., not significant. CTL, control.
Figure 1:
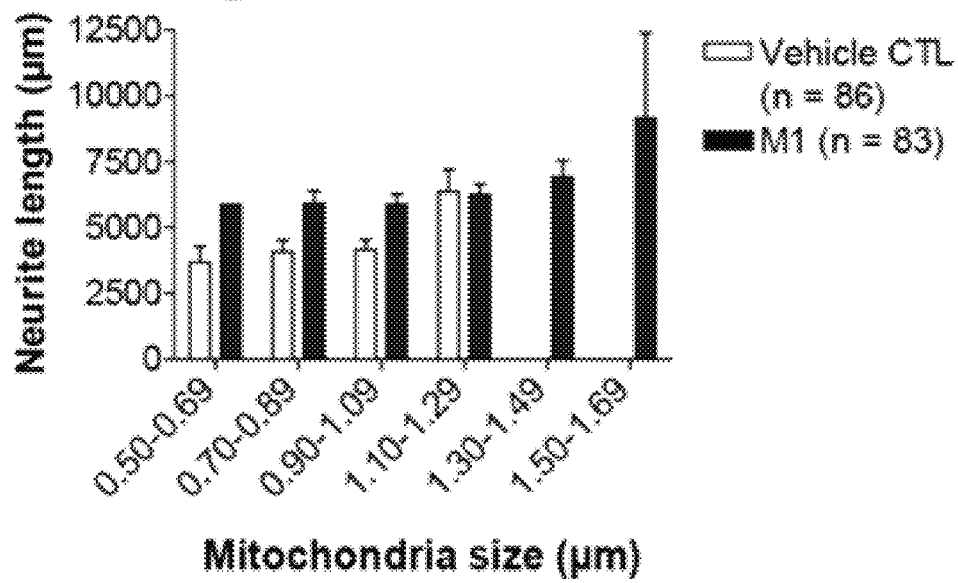
Figure 1:
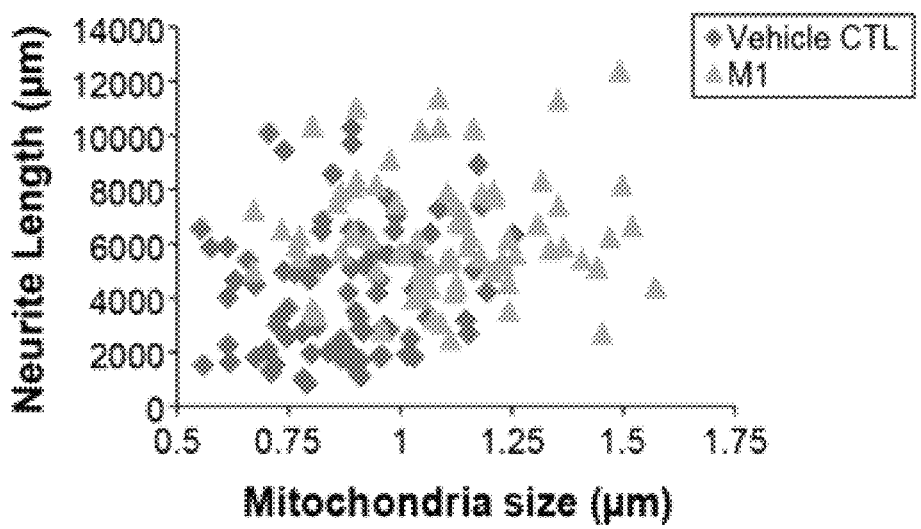

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers, but not the exclusion of any other integer or group of integers.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10%, ±7%, ±5%, ±3%, ±1%, or ±0% variation from the nominal value unless otherwise indicated or inferred.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein, the term "subject" refers to any animal (e.g., a mammal), including, but not limited to, humans, non-human primates, canines, felines, and rodents.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "optionally substituted" refers to a chemical group, such as alkyl, cycloalkyl aryl, and the like, wherein one or more hydrogen may be replaced with a with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like The term "nitro" is art-recognized and refers to $NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2$—. "Halide" designates the corresponding anion of the halogens, and "pseudohalide" has the definition set forth on 560 of "Advanced Inorganic Chemistry" by Cotton and Wilkinson.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. The present invention contemplates all such compounds, including E- and Z-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of active compound or pharmaceutical agent that elicits a biological or medicinal response in a cell culture, tissue system, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The present disclosure provides a method of treating a nerve injury in a subject in need thereof, the method comprising administering a therapeutically effective amount of a compound to the subject, wherein the compound has Formula I:

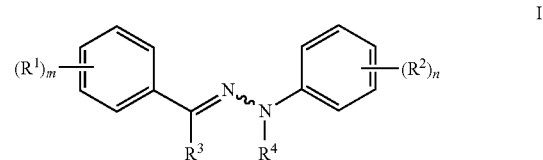

I or a conjugate salt thereof, wherein
m is a whole number selected from 1-4;
n is a whole number selected from 1-4;
$R^1$ and $R^2$ for each instance is independently selected from the group consisting of halide, nitrile, nitro, phosphate, alkyl, alkenyl, alkynyl, cycloalkyl, heterocycloalkyl, aryl, aralkyl, heteroaryl, —OR, —SR, and —$NR_2$;
$R^3$ is hydrogen or alkyl;
$R^4$ is hydrogen or alkyl; and
R for each instance is independently selected from the group consisting of hydrogen, alkyl, alkenyl, alkynyl, cycloalkyl, heterocycloalkyl, aryl, aralkyl, and heteroaryl.

The compounds described herein comprises a hydrazine moiety that can exist in the Z-isomer configuration, the E-isomer configuration, or as a mixture thereof. In certain embodiments, the compound exists in the E-isomer configuration.

Each of m and n can independently be a whole number selected from 1-4, 1-3, 2-4, 2-4, or 3-4. In certain embodiments, m is 2 and n is 3.

R for each instance can independently be hydrogen, alkyl, cycloalkyl, heterocycloalkyl, aryl, aralkyl, and heteroaryl.

R for each instance can independently be hydrogen or $C_1$-$C_6$ alkyl, $C_1$-$C_5$ alkyl, $C_1$-$C_4$ alkyl, $C_1$-$C_3$ alkyl, $C_1$-$C_2$ alkyl, or methyl.

Each of $R^1$ and $R^2$ for each instance can independently be halide, nitrile, nitro, phosphate, $C_1$-$C_6$ alkyl, $C_3$-$C_6$ cycloalkyl, $C_2$-$C_5$ heterocycloalkyl, $C_6$-$C_{10}$ aryl, $C_3$-$C_5$ heteroaryl, —OR, —SR, or —$NR_2$. In certain embodiments, each of $R^1$ and $R^2$ for each instance is independently be halide, nitrile, nitro, phosphate, $C_1$-$C_6$ alkyl, $C_1$-$C_5$ alkyl, $C_1$-$C_4$ alkyl, $C_1$-$C_3$ alkyl, $C_1$-$C_2$ alkyl, —OR, —SR, or —$NR_2$, wherein R for each instance is independently hydrogen $C_1$-$C_6$ alkyl, $C_1$-$C_5$ alkyl, $C_1$-$C_4$ alkyl, $C_1$-$C_3$ alkyl, $C_1$-$C_2$ alkyl, or methyl.

$R^3$ can be hydrogen, $C_1$-$C_6$ alkyl, $C_1$-$C_5$ alkyl, $C_1$-$C_4$ alkyl, $C_1$-$C_3$ alkyl, $C_1$-$C_2$ alkyl, or methyl. In certain embodiments, $R^3$ is hydrogen or methyl. In certain embodiments, $R^3$ is methyl.

$R^4$ can be hydrogen, $C_1$-$C_6$ alkyl, $C_1$-$C_5$ alkyl, $C_1$-$C_4$ alkyl, $C_1$-$C_3$ alkyl, $C_1$-$C_2$ alkyl, or methyl. In certain embodiments, $R^4$ is hydrogen or methyl. In certain embodiments, $R^4$ is hydrogen.

In certain embodiments the compound has Formula II:

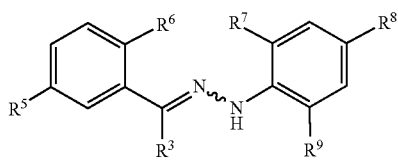

or a conjugate salt thereof, wherein each of $R^5$, $R^6$, $R^7$, $R^8$, and $R^9$ is independently selected from the group consisting of halide, nitrile, nitro, phosphate, alkyl, alkenyl, alkynyl, cycloalkyl, heterocycloalkyl, aryl, aralkyl, heteroaryl, —OR, —SR, and —NR$_2$, wherein R for each instance is independently selected from the group consisting of hydrogen, alkyl, alkenyl, alkynyl, cycloalkyl, heterocycloalkyl, aryl, aralkyl, and heteroaryl; and $R^3$ is as defined in any embodiment described herein.

In certain embodiments, $R^6$ is —OR, —SR, and —NR$_2$, wherein R for each instance is independently hydrogen, $C_1$-$C_6$ alkyl, $C_1$-$C_5$ alkyl, $C_1$-$C_4$ alkyl, $C_1$-$C_3$ alkyl, $C_1$-$C_2$ alkyl, or methyl. In certain embodiments, $R^6$ is —OR, —SR, and —NR$_2$, wherein R for each instance is independently hydrogen or methyl. In certain embodiments, $R^6$ is —OR, wherein R is hydrogen of methyl.

In certain embodiments, each of $R^5$, $R^7$, $R^8$, and $R^9$ is independently selected from the group consisting of halide, nitrile, nitro, phosphate, $C_1$-$C_6$ alkyl, $C_1$-$C_5$ alkyl, $C_1$-$C_4$ alkyl, $C_1$-$C_3$ alkyl, $C_1$-$C_2$ alkyl, and methyl. In certain embodiments, each of $R^5$, $R^7$, $R^8$, and $R^9$ is independently halide, nitrile, nitro, and methyl. In certain embodiments, $R^5$, $R^7$, $R^8$, and $R^9$ are each chloride.

In certain embodiments, the compound has the Formula III:

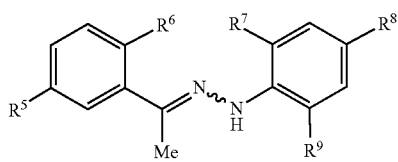

or a conjugate salt thereof, wherein each of $R^5$, $R^7$, $R^8$, and $R^9$ is independently selected from the group consisting of hydrogen, chloride, and methyl; and $R^6$ is —OR, —SR, —NR$_2$, wherein R for each instance is independently hydrogen or methyl, with the proviso that at least one of $R^7$, $R^8$, and $R^9$ is not hydrogen.

In certain embodiments, the compound has Formula III, each of $R^5$, $R^7$, $R^8$, and $R^9$ is independently selected from the group consisting of hydrogen and chloride; and $R^6$ is —OH, with the proviso that 1, 2, 3, or 4, of $R^5$, $R^7$, $R^8$, and $R^9$ is chloride.

In certain embodiments, the compound is:

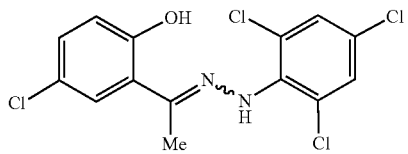 [SMILES: CC(=NNc1c(Cl)cc(Cl)cc1Cl)c1cc(Cl)ccc1O]

or a conjugate salt thereof.

The compounds described herein can readily be prepared using synthetic methodology well known in the art. For example, the compounds can be prepared by condensing an aryl hydrazine and an aryl alkyl ketone as depicted in the general synthetic sequence below.

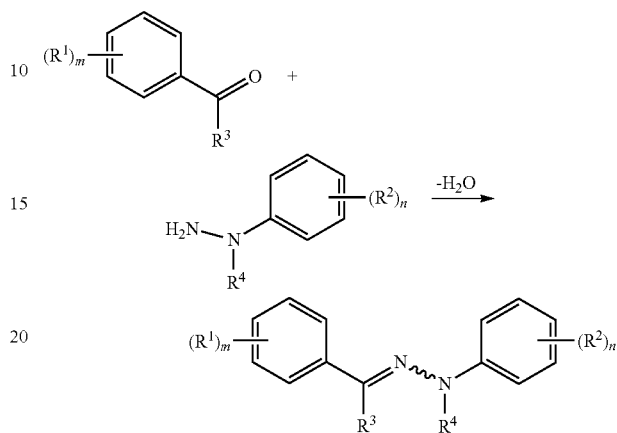

wherein m, n, $R^1$, $R^2$, $R^3$, and $R^4$ are independently as defined in any embodiment described herein. The selection of substituents and reaction conditions are well within the skill of a person of ordinary skill in the art.

The nervous system injury can comprise an injury to the central nervous system or the peripheral nervous system.

The nervous system injury can be acute or chronic. A nervous system injury can comprise the complete severing or partial severing of a neuron, or crushing or compression injury to a neuron. In certain embodiments, the nervous system injury directly impairs the normal functioning of neuron(s). In certain embodiments, the nervous system injury indirectly impairs the normal functioning of the neuron(s). The nervous system injury can result from an acute or traumatic event, chronic event, pressure build-up, or chronic neurodegeneration. Injuries to a subject can result in injury to a neuron. Common causes of nervous system injury include, but are not limited to, disease and/or infection, ischemia, anoxia, hypoglycemia, contusion, laceration, trauma to the brain or spinal cord (such as caused by acute spinal cord damage or stroke), damage by exogenous chemical agents, and combinations thereof.

The nervous system injury can be the result of a disease, disorder, or condition in a subject, such as damage to retinal ganglion cells; traumatic brain injury; stroke related injury; a cerebral aneurism related injury: a spinal cord injury, including monoplegia, diplegia, paraplegia, hemiplegia and quadriplegia; a neuroproliferative disorder or neuropathic pain syndrome.

In certain embodiments, the subject that suffers from a nervous system injury resulting from a trauma. The nervous system injury may comprise injury to the optic nerve, the spinal cord, or a peripheral nerve injury. In certain embodiments, the optic nerve comprises a retinal ganglion cell. In certain embodiments, the spinal cord injury comprises injured dorsal root ganglion neurons.

In certain embodiments, the subject suffers from a disease or condition that results in nervous system injury. In certain embodiments, the disease or condition is selected from the group consisting of stroke, spinal cord injury, Huntington's disease, Parkinson's disease, Alzheimer's disease, multiple system atrophy, spino-cerebellar atrophy, motor neuropathy, epilepsy or seizures, peripheral neuropathy, cerebral palsy, glaucoma, age related loss of neurons or neuronal connectivity and related deterioration of sensory, motor, reflect, and cognitive abilities.

In certain embodiments, the subject that suffers from an injury caused by or associated with peripheral neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

In certain embodiments, further comprises co-administration of a therapeutically effective amount of a Pten inhibitor to the subject. In certain embodiments, the Pten inhibitor is an antibody, an antibody fragment (such as Fab, Fab', F(ab')$_2$, and Fv), single chain (ScFv)), protein, polypeptide, interfering RNA (RNAi), an aptamer, or a small molecule. Exemplary Pten inhibitors include, but are not limited to, deltamethrin, sodium alendronate, N-(9,10-dioxo-9,10-dihydrophenanthren-2-yl)-2,2-dimethylpropionamide, 5-benzyl-3furylmethyl (1R,S)-cis,trans-chrysanthemate, sodium suramin, 4-methoxyphenacyl bromide, 1,4-dimethylendothall, 1,4-dimethyl-7-oxabicyclo[2.2.1]heptane-2,3-dicarboxylic acid, cantharidic acid; 2,3-dimethyl-7-oxabicyclo[2.2.1]heptane-2,3dicarboxylic acid, sodium Stibogluconate; antimony sodium gluconate, ethyl-3,4-dephostatin, fenvalerate, sodium α-naphthyl acid phosphate, sodium β-glycerophosphate, endothall, and cypermethrin.

A compound described herein and a Pten inhibitor may be administered concurrently (e.g., simultaneously, essentially simultaneously or within the same treatment protocol) or sequentially, depending upon the nature of the nervous system injury, the condition of the subject, and the actual choice of the Pten inhibitor to be administered in conjunction (i.e., within a single treatment protocol) with a compound described herein.

If a compound described herein and the Pten inhibitor are not administered simultaneously or essentially simultaneously, then the optimum order of administration of the compound described herein and the Pten inhibitor, may be different for different types of nervous system injuries. Thus, in certain situations the compound described herein may be administered first followed by the administration of the Pten inhibitor; and in other situations the Pten inhibitor may be administered first followed by the administration of a compound described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject.

Administration of a compound described herein to the subject can be by any one or combination of a variety of methods. The appropriate method(s) will depend upon the circumstances of the individual (e.g. the location of the nervous system injury or target neuron(s), the condition of the individual, the desired duration of the contact, whether local or systemic treatment is desired). The administration can be by any methods described herein that will result in contact of sufficient amount of a compound described herein to the target neuron to induce a therapeutic effect. For example, parenteral, enteral and topical administration can be used. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Enteral administration involves the esophagus, stomach, and small and large intestines (i.e., the gastrointestinal tract). The phrases "systemic administration," "administered systemically", "peripheral administration" and "administered peripherally" as used herein mean the administration of a compound other than directly into the central nervous system, such that it enters the animal's system and, thus, is subject to metabolism and other like processes, for example, subcutaneous administration. Administration may be topical (including ophthalmic), oral or pulmonary administration, e.g., by inhalation or insufflation, or intracranial, e.g., intrathecal or intraventricular, administration, topically to the eye, or by intraocular injection.

In certain embodiments, the compounds described herein are administered to the subject by any one or a combination of methods selected from the group consisting of intravitreally, intraperitoneally, suprachoroidally, subconjunctivally, retrobulbarly, intracamerally, and subretinally. In certain embodiments, the compounds described herein are administered to the subject intravitreally.

In certain embodiments, the compounds are administered to the eye. In instances in which the compound is administered to the eye, the route of administration can be selected from intravitreal injection, topical, intracameral injection, subconjunctival injection, sub-tenon injection, retro bulbar injection, sub-retinal injection, and peri-ocular or laterobulbar injection.

Specific routes of administration and the dosage regimen will be determined by skilled clinicians, based on factors such as the exact nature of the condition being treated, the severity of the condition, and the age and general physical condition of the patient.

The present disclosure also provides a method of promoting growth, regrowth, and/or regeneration of a neuron, the method comprising contacting the neuron with a therapeutically effective amount of a compound described herein. Contacting the neuron can occur in vivo, in vitro or ex vivo. Neuron cells can be isolated from a subject and grown in vitro, using techniques well known in the art. The neuron may be a healthy neuron or an injured neuron. The neuron cell can be a central nervous system neuron or a peripheral nervous system neuron. In certain embodiments, the neuron cell is a retinal ganglion cell or a dorsal root ganglion neuron.

In certain embodiments, the method comprises: contacting the injured neuron with a compound described herein.

The neuron cell may be isolated from a subject that suffers from a disease or condition that results in nervous system injury. In certain embodiments, the disease or condition is selected from the group consisting of stroke, spinal cord injury, Huntington's disease, Parkinson's disease, Alzheimer's disease, multiple system atrophy, spino-cerebellar atrophy, motor neuropathy, epilepsy or seizures, peripheral neuropathy, cerebral palsy, glaucoma, age related loss of neurons or neuronal connectivity and related deterioration of sensory, motor, reflect, and cognitive abilities.

The neuron cell may be isolated from a subject that suffers from an injury caused by or associated with peripheral neuropathies, such as diabetic neuropathy, virus-associated neuropathy, botulism-related neuropathy; toxic polyneuropathy, nutritional neuropathy, angiopathic neuropathy, sarcoid-associated neuropathy; carcinomatous neuropathy; compression neuropathy, and/or hereditary neuropathy; and/or peripheral nerve damage associated with spinal cord injury.

The neuron cell may be isolated from a subject that suffers from a neurological injury resulting from a trauma. The neurological injury may comprise injury to the optic nerve, the spinal cord, or a peripheral nerve injury.

Treatment of the neuron cell may result in one or more of the growth or regeneration of the injured neuron.

A class of diaryl hydrazone mitochondrial fusion promoters, exemplified by M1, are useful in therapeutic intervention to enhance intrinsic growth capacity of adult neurons. This is an important step as successful axon regeneration after nervous system injuries largely depends on the intrinsic growth capacity of injured neurons.

Knockout of mitochondrial fusion protein Mfn1 or Mfn2 resulted in mitochondrial fragmentation, early sign of apoptosis, which was completely restored by M1 treatment in MEF $Mfn1^{-/-}$ or $Mfn2^{-/-}$ cultures. M1 treatment protected dopaminergic neuron-like SH-SY5Y cells from 1-methyl-4-phenyl-pyridinium (MPP+)-induced neurotoxicity as implicated in PD pathogenesis. It was examined if shifting the mitochondrial fusion/fission equilibrium using mitochondrial fusion promoter M1 could eventually increase the intrinsic growth capacity of adult peripheral (i.e. dorsal root ganglion; DRG) neurons. The therapeutic potential of M1 in promoting axonal regrowth in adult DRG neurons was first investigated. The results demonstrated that M1 and analogs thereof can increase 49% neurite outgrowth from adult DRG neurons with no cell survival effect (FIG. 1A). Further analysis showed that the length of regenerating axon was directly proportional to the size of mitochondria (FIG. 1B).

Figure 2:
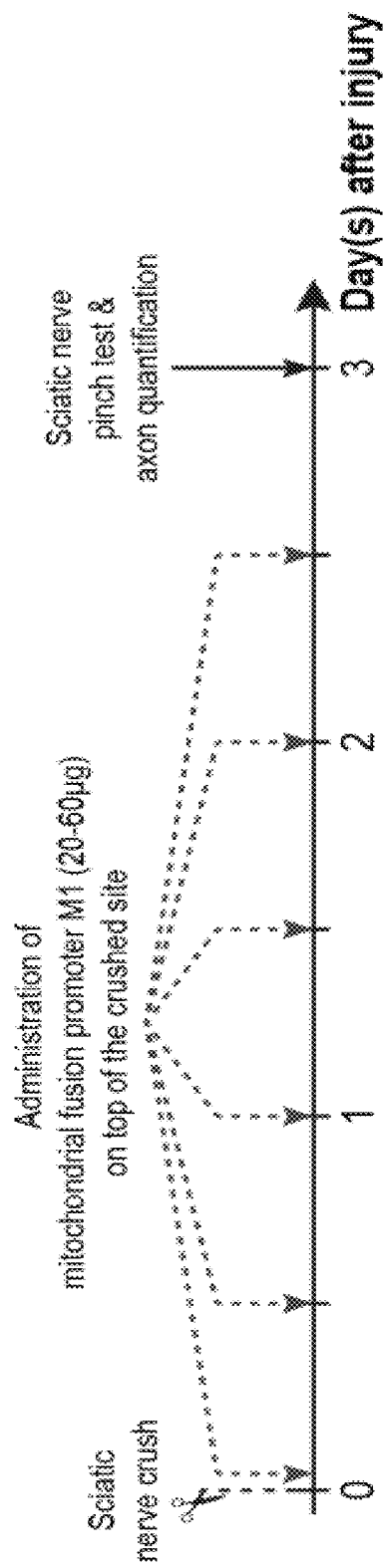
FIG. 2 depicts an experimental paradigm for assessing the growth-promoting effects of mitochondrial fusion promoter M1 after peripheral nerve injury. Sciatic nerve crush injury was performed on adult male C57BL/6 mice. Immediately after crush, 20-60 μg of mitochondrial fusion promoter M1 was directly applied on top of the crushed site, followed by a total of 6 administrations (i.e. morning and evening administration with at least 8 hours apart). Sciatic nerve pinch test and axon quantification were performed on day 3 post-injury.
Figure 3:
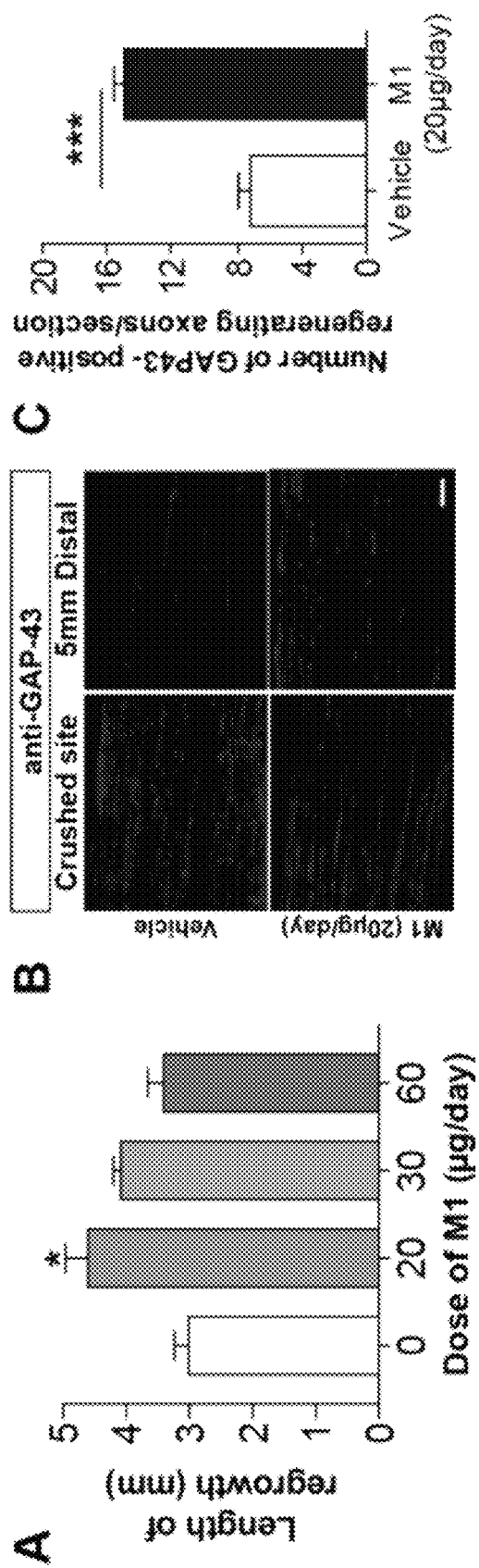
FIG. 3 depicts data showing that mitochondrial fusion promoter M1 accelerates in vivo axonal regrowth after sciatic nerve crush injury in adult mice. Sciatic nerve crush injury was performed on adult C57BL/6 mice (8-12 weeks old). A total of 6 administrations of mitochondrial fusion promoter M1 was directly applied to the crushed site for 3 consecutive days. Sciatic nerve pinch test and axon quantification were performed 3 days after injury. (A) Treating the mice with mitochondrial fusion promoter M1 markedly increased the distal extent of axonal regrowth 3 days after injury as determined by sciatic nerve pinch test, with its maximal effects at 20 μg/day (n=3-6 per group). (B and C) More GAP-43-positive regenerating axons was found at 5 mm distal to the crushed site in M1-treated mice compared with vehicle controls (n=3 per group). Scale bar: 50 μm. Mean±SEM. *P<0.05, ***P<0.001; one-way ANOVA followed with Bonferroni post-hoc test in (A), Student's t-test in (C).

These findings were extended to in vivo studies of nerve regeneration after peripheral and central nerve injuries. 20-60 μg of M1 (in 2% DMSO) was applied directly onto the crushed site immediately after sciatic nerve crush injury, followed by a total of 6 administrations for 3 consecutive days (i.e. morning and evening administration with at least 8 hours apart) (see FIG. 2 for detailed experimental paradigm). In line with the in vitro results, it was shown that the most distal axonal regrowth was increased by 55% 3 days after injury (FIG. 3A). The number of regenerating axons [Growth Associate Protein (GAP)-43 positive] was increased by 2-fold as compared to vehicle controls (FIG. 3B). These results confirmed the therapeutic potential of M1 in axon regeneration in vivo.

Figure 4:
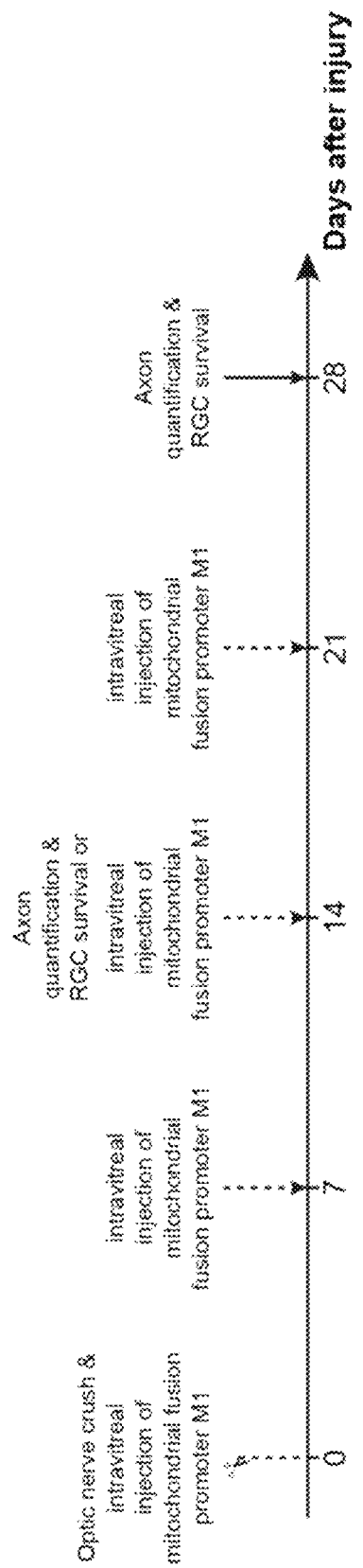
FIG. 4 depicts an experimental paradigm to assess axon regeneration and retinal ganglion cell (RGC) survival after optic nerve crush injuries. Immediately after optic nerve crush injury, adult male C57BL/6 mice (8-12 weeks old) were intravitreally injected with 1 μg of mitochondrial fusion promoter M1 once per week for 2 weeks (i.e. days 0 and 7) or 4 weeks (i.e. days 0, 7, 14 and 21). Three days before termination, mice were intravitreally injected with cholera toxin subunit B conjugated with Alexa Fluor 555 (CTB-555) to anterograde label regenerating axons, and optic nerves were treated with benzyl benzoate/benzyl alcohol (2:1) for tissue clearance. Serial transverse cryosections (20 μm) of retinae were immunostained with anti-RBPMS primary antibodies for RGC survival. RBPMS-positive RGCs were counted in every fifth section per retinae (3-5 sections). Axon quantification and RGC survival were performed on days 14 and 28 post-injury.
Figure 5:
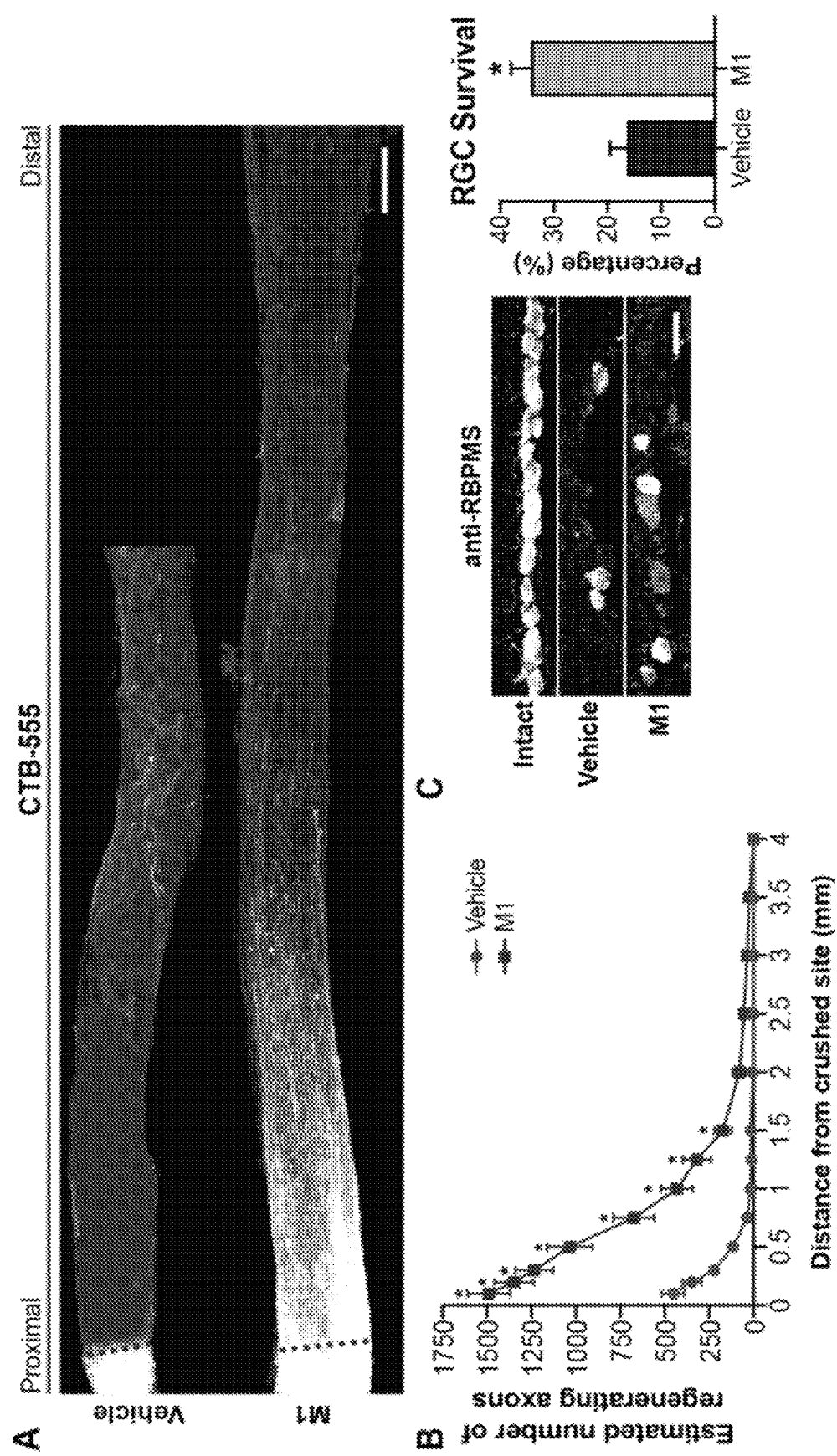
FIG. 5 depicts data showing that intravitreal injections of mitochondrial fusion promoter M1 induces robust axon regeneration 14 days after optic nerve crush injury. 1 μg of M1 (1 μg/μl) was intravitreally injected into the injured eye at day 0 and 7 after optic nerve crush injury. Three days before termination, 2 μg of CTB-555 was intravitreally injected to anterograde label the regenerating axonal fibres. (A and B) While virtually no regenerating axons were observed in vehicle-treated controls, M1 treatment induced robust axon regeneration 14 days after injury. Mean±SEM (n=5-7 per group). *P<0.05, Student's t-test. (C) More RBPMS-positive RGCs were observed in M1-treated mice, compared with vehicle-treated controls. Scale bars: 200 μm in (A), 20 μm in (C).
Figure 6:
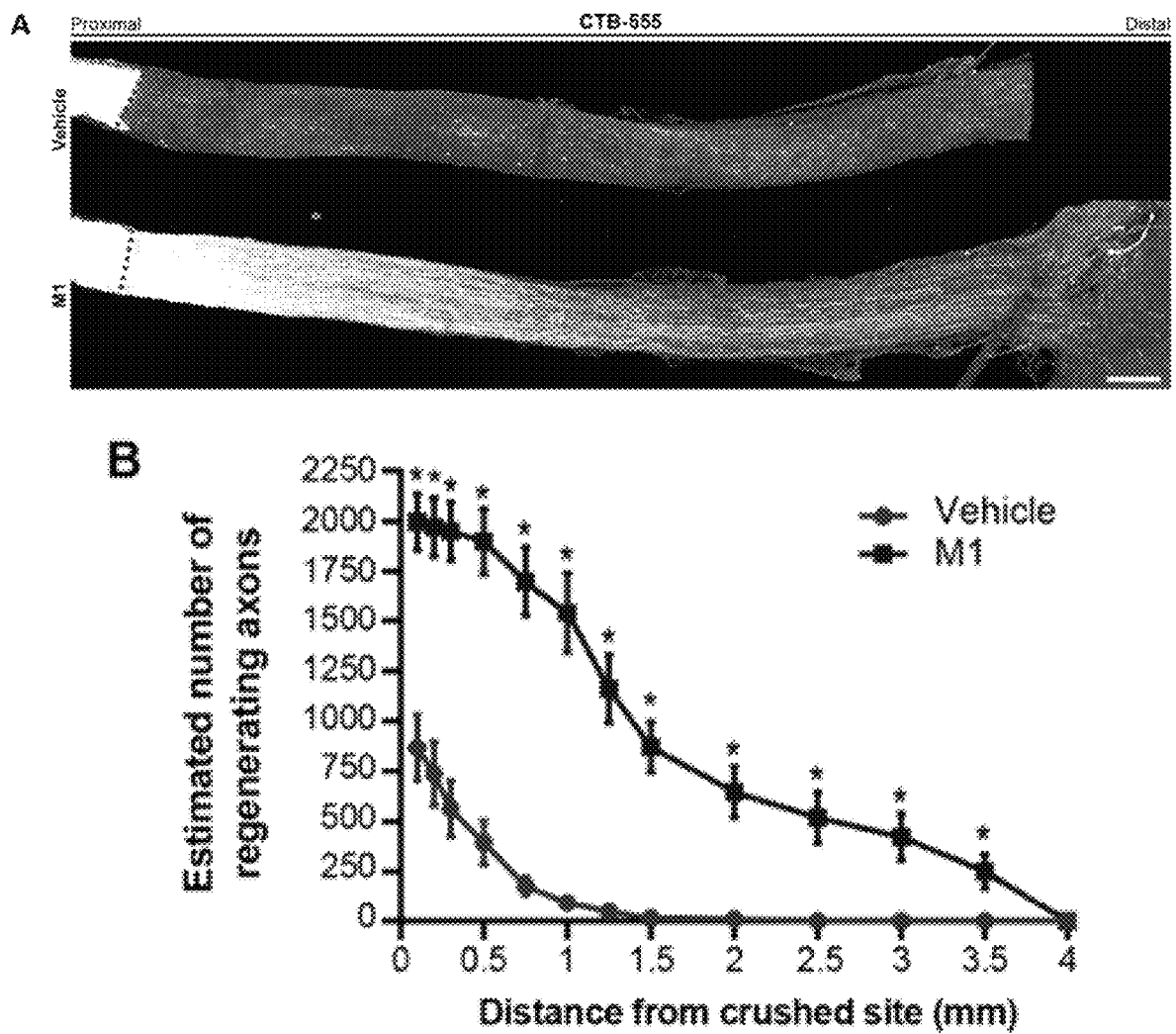
FIG. 6 depicts data showing that mitochondrial fusion promoter M1 induces long-distance axon regeneration 28 days after optic nerve crush injury. 1 μg of M1 (1 μg/μl) was intravitreally injected into the injured eye at day 0, 7, 14 and 21 after optic nerve crush injury. Three days before termination, 2 μg of CTB-555 was intravitreally injected to anterograde label the regenerating axonal fibres. (A and B) M1 treatment induced substantial axonal regrowth 28 days after optic nerve crush injury. Mean±SEM (n=5-7 per group). *P<0.05, Student's t-test. (C) Some of the regenerating axonal fibres (yellow arrowheads) regenerated to the optic chiasm (OX). (D) More RBPMS-positive RGCs were observed in M1-treated mice, compared with vehicle-treated controls. Scale bars: 200 μm in (A and C), 20 μm in (D).
Figure 6:
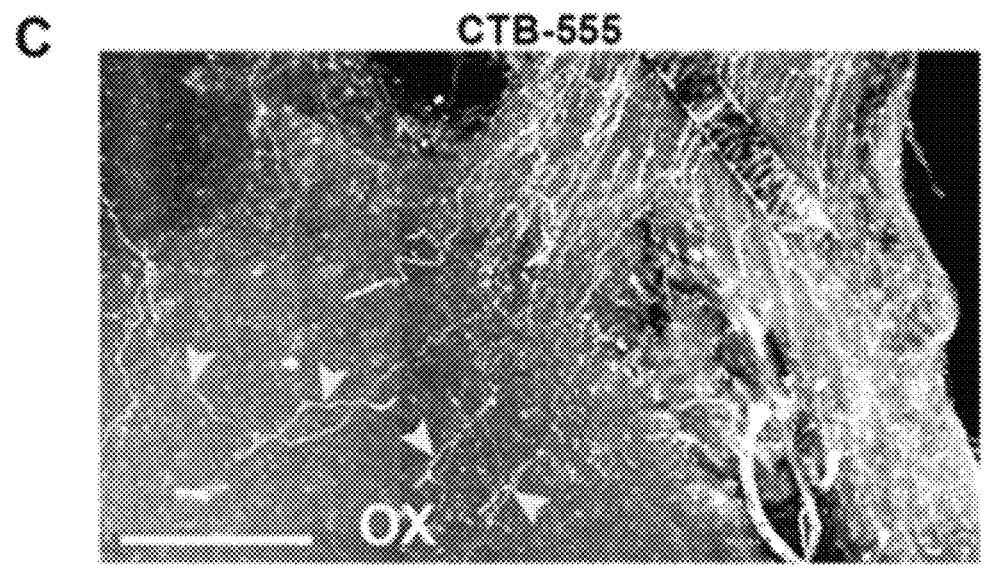
Figure 6:
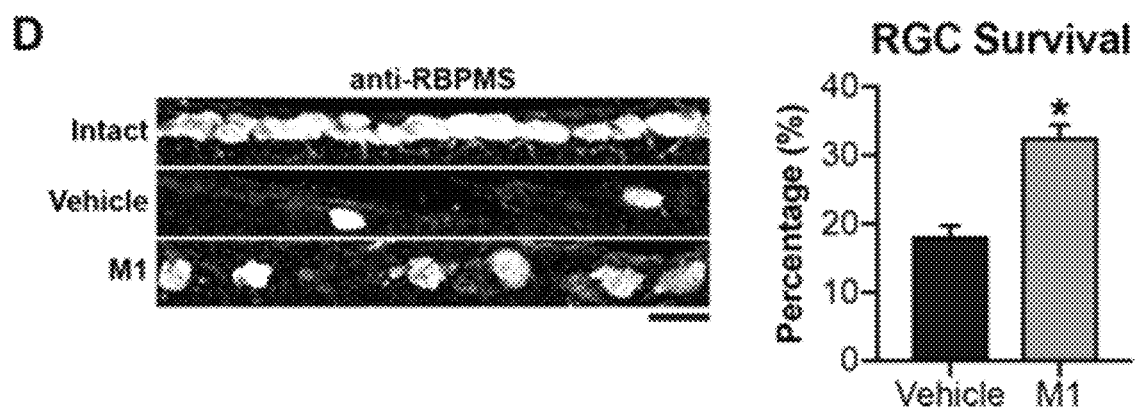

Next, it was tested whether mitochondrial fusion promoter M1 could also promote axon regeneration after optic nerve crush injury, a well-established animal model of CNS injury. M1 was intravitreally injected into the injured eye at days 0, 7 (for 14 days), 14 and 21 (for 28 days), and the extent of axon regeneration was assessed at day 14 and 28 after injury, respectively (see FIG. 4 for detailed experimental paradigm). In vehicle-treated mice, there is virtually no regenerating fibers observed even after 28 days of injury. In contrast, mice treated with M1 induced robust axon regeneration at 14 (FIGS. 5A and 5B) and 28 (FIGS. 6A and 6B) days after injury. Some of the regenerating axons could actually reach the optic chiasm at day 28 post-injury (FIG. 6C). In parallel, more retinal ganglion cells (RGCs) were survived 14 (FIG. 5C) and 28 days (FIG. 6D) after optic nerve crush injury, suggesting that M1 is a potent small molecule to promote axonal regrowth after central and peripheral nerve injuries.

To evaluate whether regenerating axons are sufficient to induce neuronal firing from the superior colliculus by optogenetics approach, local field potential (LFP) recordings in superior colliculus (SC) were performed after optical stimulation in the retinal ganglion cell (RGCs) of the injured eye. To record evoked LFP in SC, mice received intravitreal injection of AAV-ChR2-mCherry 2 weeks after crush. Six weeks after optic nerve crush injury, we stimulated the injured RGCs by placing an optical fiber with blue laser at 473 nm illuminated at the periphery of the left eye (injured). Evoked LFPs in response to the optical stimuli from ChR2-overexpressing RGCs were recorded in the SC. There were virtually no LFP amplitudes that could be detected from the vehicle-treated mice (FIG. 7A), which was consistent with the histology results. In contrast, significantly higher LFP amplitudes from M1-treated mice (59.82±3.6 μV) compared with vehicle-treated controls (13.75±1.61 μV) (FIG. 7B) could not be detected. By combining M1 with Pten deletion which is known to induce axon regeneration after CNS injury, significantly larger RMS LFP amplitudes from Pten-knockout (Pten-KO) and M1-treated mice (88.36±3.13 μV) compared with M1-treated mice were detected. Treating the mice with M1 and Pten deletion restored almost 25% of the maximal LFP amplitude compared with uninjured mice.

Experiments

Assessing the Intrinsic Growth Capacity of Peripheral Neurons after Treating with Mitochondrial Fusion Promoter M1:

The current study aimed to investigate the therapeutic potential of mitochondrial fusion promoter M1 for treating patients with nerve injuries. First, we examined if mitochondrial fusion promoter M1 could enhance the intrinsic growth capacity of adult neurons, a critical determinant for successful axon regeneration after nerve injuries. We used primary cultures of axotomized dorsal root ganglion (DRG) neurons as an in vitro model to assess the extent of neurite outgrowth after treating the neurons with mitochondrial fusion promoter M1. Primary cultures of DRG neurons were prepared from adult C57BL/6 mice (8-12 weeks old). The DRG neurons were first dissected out, digested with collagenase/dispase II solution (Roche Diagnostics), trypsinized and dissociated mechanically by three flame-polish Pasteur pipettes with different diameters. Two thousand DRG neurons were plated onto a poly-D-lysine and laminin-coated 8-well chamber (Millipore), and cultured in full Neurobasal medium (Gibco) supplemented with B27, 200 mM L-glutamine, penicillin-streptomycin, 50 ng/ml NGF (Gibco), 10 μM Ara-C and 2 ng/ml GDNF (Gibco). Mitochondrial fusion promoter M1 was first dissolved in 100% DMSO, and added into the cultured neurons at a final concentration of 2.5 μM one hour after plating. 0.1% DMSO was used as vehicle controls.

After growing the cultures for 17 hours, the cultured neurons were fixed with 4% paraformaldehyde (PFA), blocked with 0.5% bovine serum albumin (BSA)/0.1% Triton X-100 in PBS for 1 hour, and incubated with anti-βIII-tubulin primary antibodies (1:800, Sigma Aldrich) for overnight at 4° C. After washing with PBS for three times, the cultures were incubated with corresponding secondary antibodies conjugated with Alexa Fluor 488 (1:300, Molecular Probes) for 1 hour.

For neurite outgrowth assay, 30 non-overlapping images were captured at 10× magnifications using Nikon Ni-E epifluorescence microscope equipped with a motorized stage. Total neurite length of each neuron from each condition were automatically measured using WIS-NeuroMath software (Weizmann Institute of Science). At least 250 neurons were quantified from each condition to obtain the average total neurite length. Data were obtained from three separated experiments repeated in duplicates (FIG. 1).

Animal Model of Peripheral Nerve Injury:

We performed sciatic nerve crush injury (an in vivo animal model for peripheral nerve injury) on adult male C57BL/6 mice (8-12 weeks old) to assess the extent of axon regeneration after peripheral nerve injury. All mouse husbandry and euthanasia were in compliance with the Institutional Animal Care and Use Committee (IACUC) guidelines. Surgical procedures performed were in accordance with protocols approved by the City University of Hong Kong Animal Research Ethics Sub-Committee and Department of Health, Hong Kong SAR. The mice were first anesthetized with 2.5% isoflurane, and the left sciatic nerve was exposed. After separating the nerve from the surrounding connective tissue, the left sciatic nerve was crushed with 5/45 smooth forceps (Fine Science Tools) for 15 seconds at the level of external rotator muscles, just distal to the sciatic notch.

Treatment Paradigm of Mitochondrial Fusion Promoter M1 after Peripheral Nerve Injury:

Mitochondrial fusion promoter M1 was first dissolved in DMSO, and 20-60 μg (at a final volume of 30 μl) of M1 was directly applied on top of the crushed site immediately after sciatic nerve crush injury, followed by a total of 6 administrations for 3 consecutive days (i.e. morning and evening administrations per day with time interval of 8 hours apart) (see FIG. 2 for detailed experimental paradigm).

Assessment of the Extent of Axon Regeneration Following Peripheral Nerve Injury:

We first confirmed the growth-promoting effects of mitochondrial fusion promoter M1 using sciatic nerve pinch test. The results from sciatic nerve pinch test were subsequently verified by quantifications of GAP-43-positive regenerating axons 3 days after sciatic nerve crush injury.

Sciatic Nerve Pinch Test:

Following the completion of dosing paradigm of M1, sciatic nerve pinch test was performed on the ipsilateral nerves 3 days after sciatic nerve crush injury. Under deep anesthesia (2.5% isoflurane), the left sciatic nerve was exposed to mid-thigh level, and the mice was gradually recovered from anesthesia which allow them to respond from pinches. Under light anesthesia (i.e. 1% isoflurane), a series of pinches were directly applied to the ipsilateral nerve from the most distal site (i.e. trifurcation), moving proximally towards the crushed site using 5/45 smooth forceps (Fine Science Tools). The distance (in mm) was recorded from the crushed site to the most distal point of the nerve where initial withdrawal response was generated after pinching (FIG. 3A).

Quantification of Regenerating Axons and Retinal Ganglion Cell (RGC) Survival after Optic Nerve Injury:

We used cholera toxin subunit B (CTB) to anterograde label the regenerating axons after optic nerve crush injury. Three days before termination, 5 2 μg of Alexa Fluor 555-conjugated CTB (i.e. CTB-555) was intravitreally injected to the injured eye using a glass micropipette inserted to the periphery of the retinae. After 3 days of injection, the optic nerves were dissected out and post-fixed with 4% PFA. The nerves were first incubated with increasing concentrations of ethanol (i.e. 50%, 80% and 95%) for 20 minutes with constant agitation at room temperature, and incubated with absolute (i.e. 100%) ethanol for overnight at 4° C. On the next day, the nerves were incubated with 100% hexane for 3 hours to remove any remaining water droplets in the nerves. Finally, the nerves were cleared with benzyl alcohol and benzyl benzoate solution at a ratio of 1:2. In general, the nerves turned transparent within 1-2 minutes, and the cleared nerves were mounted on a microscope slide with clearing solution. The images of the whole nerve were captured at 20× magnifications using Carl Zeiss LSM 880 confocal microscope equipped with AiryScan Fast Mode and a motorized stage, with optical sections of 1.7 μm. The images were then stitched and maximum projected using ZEN2.3 Blue Software (Carl Zeiss) (FIG. 5A; FIG. 6A).

To determine the extent of axonal regrowth after treatment of mitochondrial fusion promoter M1, the average number of CTB-555-positive axons were quantified by counting the number of CTB-positive axons extending across different nerve segments distal to the crushed site in 3-5 optical sections (10-μm-thick) from each mouse. The diameter of the nerve was measured at each point where the counting was performed (FIG. 5B; FIG. 6B). The estimated number of regenerating axons ($\Sigma a_d$) extending to the distance d, was calculated using the formula as shown below:

$$\Sigma a_d = \pi r^2 \times [\text{average axons/mm}]/t$$

t=thickness of the section (i.e. 10 μm)

To determine RGC survival after optic nerve crush injury, the eyeballs from both contralateral and ipsilateral side were dissected out, post-fixed with 4% PFA, cryoprotected and frozen in O.C.T. compound. The eyeballs were cut longitudinally into 20-μm-thick serial cryosections, blocked with 0.5% BSA/0.5% Triton X-100 for 1 hour, and incubated with anti-RBPMS primary antibodies (1:500, Abcam) for overnight. After washing with PBS, the cryosections were incubated with Alexa Fluor 647-conjugated secondary antibodies (1:300, Molecular Probes) for 2 hours. For each section of retina, 2-3 images were captured at 40× magnifications using Carl Zeiss LSM 880 confocal microscope equipped with AiryScan Fast Mode and a motorized stage. The number of RBPMS-positive RGCs were manually counted from every fifth sections from both contralateral (i.e. uninjured) and ipsilateral (i.e. injured) retinae (3-5 sections per retina), respectively, using ImageJ software with Cell Counter plugin. The percentage of RGC survival in the ipsilateral retinae was normalized with the mean number of RBPMS-positive RGCs from the contralateral retinae of the same mice (FIG. 5C; FIG. 6C).

Optogenetic Stimulation of RGCs and Local Field Potential (LFP) Recordings from Superior Colliculus To optically stimulate the RGCs in vivo, AAV expressing a fusion of channelrhodopsin-2 and mCherry (AAV-ChR2-mCherry) at viral titre of $1 \times 10^{13}$ vg/ml was injected intravitreally into both eyes two weeks before optogenetics experiments. For intravitreal injection, a micropipette was gently inserted into the peripheral retina of the eye, just behind the ora serrata, placed with an angle to avoid damages to the lens. One microliter of AAV-ChR2-mCherry was infused at a constant slow rate of 200 nl/min to avoid damages to the eyeball. Overexpression of ChR2-mCherry allows optical stimulation of the transduced RGCs under illumination at 473 nm.

Figure 7:
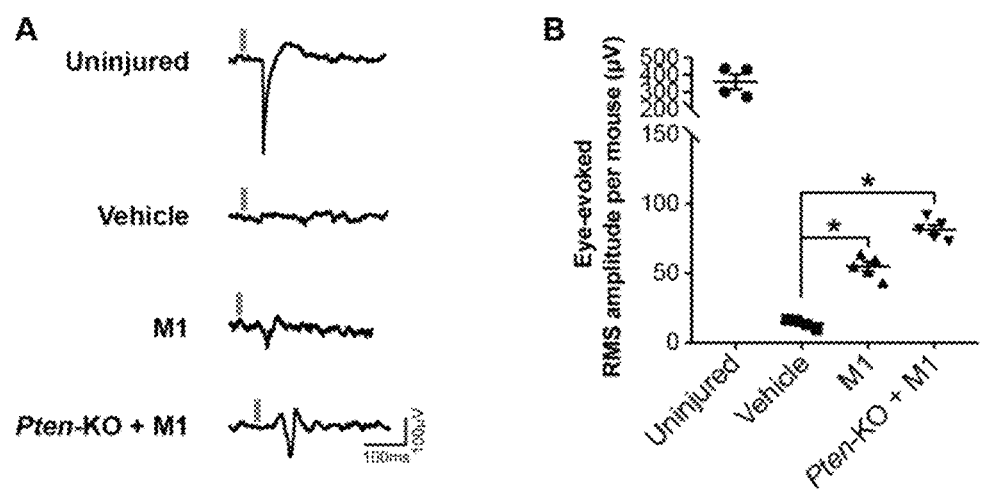
FIG. 7 depicts data showing that the regenerated axons in M1-treated mice can conduct action potentials detected by local field potential (LFP) recordings in superior colliculus. Two weeks before LFP recordings, AAV overexpressing a fusion of channelrhodopsin 2 and mCherry was injected into the injured eye of the mice. During LFP recordings, the RGCs from the injured eye were optically stimulated at a wavelength of 473 nm, and the LFP amplitudes were recorded in superior colliculus. (A) While virtually no LFP amplitudes could be detected from vehicle-treated mice, M1-treated mice evoked distinct LFPs detected in superior colliculus after optical stimulation of injured RGCs. Blue lines indicated optical stimulation in the injured eye. (B) Eye-evoked root-mean-square (RMS) LFP amplitudes were automatically determined using Spike2 software with customized MATLAB program. Administration of M1 markedly elevated the eye-evoked RMS LFP amplitudes compared with vehicle-treated controls. Combination of phosphatase and tensin homolog (Pten) deletion and M1 treatment further increased the RMS LFP amplitudes after optical stimulations of injured RGCs. Mean±SEM (n=4-5 per group). *P<0.05, one-way ANOVA with Bonferroni post-hoc test.

For LFP recordings in superior colliculus, a midline skin incision was performed on anesthetized mice to expose the skull, and craniotomy was performed at 5 mm lateral and rostral to the lambda suture of the right hemisphere. A 16-channel recording microelectrode was placed on the cortical layer of the superior colliculus and grounding electrode was placed on the frontal bone. After cleaning and application of eye gel to the injured eye, an optical fibre connected to a laser source at 473 nm was placed at the periphery of the injured eye to stimulate the RGCs, and the eye-evoked LFP amplitudes were recorded 5 in the superior colliculus using the data acquisition system (Bio-Signal Technologies) with preset analog filters (high-pass filter: 0.3 Hz; low-pass filter: 100 Hz), sampled at 100 Hz, and digitally filtered (low-pass FIR filter: 25 Hz). The data recorded from the system was used as digital input signals for synchronization of the optogenetics setup. Data were analyzed offline using spike2 software (Version 8) and customized MATLAB program. Root-mean-square (RMS) amplitudes after optical stimulation was calculated (FIG. 7).

According to the present invention, the mitochondrial fusion promoter M1 can be directly applied to the injured site of patients to promote axonal regrowth after peripheral nerve injury. Also, intravitreal injections of M1 on a weekly basis successfully induce substantial axonal regrowth after optic nerve crush injury. It is thus believed that the local administration of M1 can be used as a treatment for patients with PNS and CNS injuries so as to promote axon regeneration and functional recovery.

INDUSTRIAL APPLICABILITY

The diaryl hydrazones described herein are useful therapeutic agents in the treatment of injured nerve cells and nerve injuries in a subject in need thereof.

What is claimed is:

1. A method of treating a nerve injury in a subject in need thereof, the method comprising administering a therapeutically effective amount of a compound to the subject, wherein the compound has Formula I:

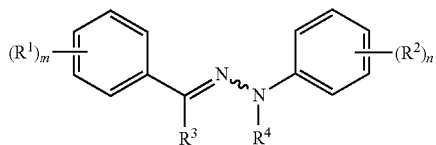

or a conjugate salt thereof, wherein
m is a whole number selected from 1-4;
n is a whole number selected from 1-4;
$R^1$ and $R^2$ for each instance is independently selected from the group consisting of halide, nitrite, nitro, phosphate, alkyl, alkenyl, alkynyl, cycloalkyl, heterocycloalkyl, aryl, aralkyl, heteroaryl, —OR, —SR, and —NR$_2$;
$R^3$ is $C_1$-$C_6$ alkyl;
$R^4$ is hydrogen or alkyl; and
R for each instance is independently selected from the group consisting of hydrogen, alkyl, alkenyl, alkynyl, cycloalkyl, heterocycloalkyl, aryl, aralkyl, and heteroaryl.

2. The method of claim 1, wherein $R^4$ is hydrogen.

3. The method of claim 1, wherein $R^1$ and $R^2$ for each instance is independently halide, nitrite, nitro, phosphate, —OR, —SR, and —NR$_2$, wherein R for each instance is independently hydrogen or alkyl.

4. The method of claim 1, wherein $R^1$ and $R^2$ for each instance is independently halide or hydroxyl.

5. The method of claim 1, wherein m is a whole number selected from 1-2; n is a whole number selected from 1-3; $R^1$ and $R^2$ for each instance is independently halide, nitrite, nitro, phosphate, —OR, —SR, and —NR$_2$, wherein R for each instance is independently hydrogen or alkyl; $R^3$ is $C_1$-$C_6$ alkyl; and $R^4$ is hydrogen.

6. The method of claim 5, wherein the compound has the Formula II:

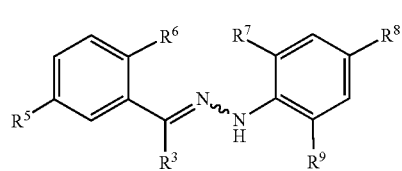

or a conjugate salt thereof, wherein each of $R^5$, $R^6$, $R^7$, $R^8$, and $R^9$ is independently halide, nitrile, nitro, phosphate, methyl, —OR, —SR, or —NR$_2$, wherein R for each instance is independently hydrogen or alkyl; and $R^3$ is $C_1$-$C_6$ alkyl.

7. The method of claim 6, wherein each of $R^5$, $R^6$, $R^7$, $R^8$, and $R^9$ is independently halide, methyl, or OR, wherein R for each instance is independently hydrogen or $C_1$-$C_6$ alkyl.

8. The method of claim 6, wherein $R^3$ is methyl.

9. The method of claim 1, wherein the compound is:

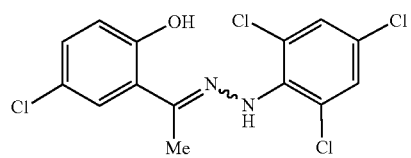 [SMILES: CC(=NNc1c(Cl)cc(Cl)cc1Cl)c1cc(Cl)ccc1O]

or a conjugate salt thereof.

10. The method of claim 1, wherein the nerve injury comprises at least one of a central nervous system injury or a peripheral nervous system injury.

11. The method of claim 1, wherein the compound promotes the regrowth of injured axons.

12. The method or claim 1, wherein the compound is administered intravitreally, intraperitoneally, suprachoroidally, subconjunctivally, retrobulbarly, intracamerally, or subretinally.

13. The method of claim 1, wherein the compound is co-administered with a therapeutically effective amount of a phosphatase and tensin homolog (Pten) inhibitor.

14. The method of claim 1, wherein the compound is:

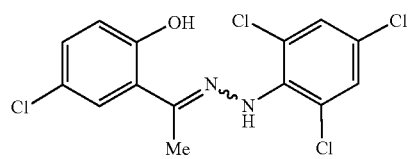 [SMILES: CC(=NNc1c(Cl)cc(Cl)cc1Cl)c1cc(Cl)ccc1O]

or a conjugate salt thereof.

15. A method of treating an injured neuron, the method comprising contacting the injured neuron with a compound, wherein the compound has Formula I:

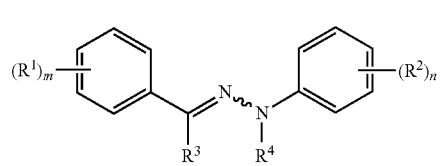

or a conjugate salt thereof, wherein m is a whole number selected from 1-4;

n is a whole number selected from 1-4;

$R^1$ and $R^2$ for each instance is independently selected from the group consisting of halide, nitrile, nitro, phosphate, alkyl, alkenyl, alkynyl, cycloalkyl, heterocycloalkyl, aryl, aralkyl, heteroaryl, —OR, —SR, and —$NR_2$;

$R^3$ is $C_1$-$C_6$ alkyl;

$R^4$ is hydrogen or allyl; and

R for each instance is independently selected from the group consisting of alkyl, alkenyl, alkynyl, cycloalkyl, heterocycloalkyl, aryl, aralkyl, and heteroaryl, wherein the step of contacting the injured neuron occurs in vitro or ex vivo.

16. The method of claim 15, wherein m is a whole number selected from 1-2; n is a whole number selected from 1-3; $R^1$ and $R^2$ for each instance is independently halide, nitrile, nitro, phosphate, —OR, —SR, and —$NR_2$, wherein R for each instance is independently hydrogen or alkyl; $R^3$ is $C_1$-$C_6$ alkyl; and $R^4$ is hydrogen.

17. The method of claim 16, wherein the compound has the Formula II:

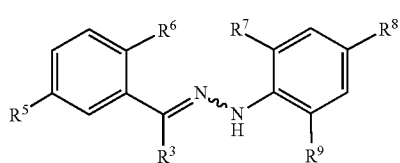

or a conjugate salt thereof, wherein each of $R^5$, $R^6$, $R^7$, $R^8$, and $R^9$ is independently halide, nitrile, nitro, phosphate, methyl, —OR, —SR, or —$NR_2$, wherein R for each instance is independently hydrogen or alkyl; and $R^3$ is $C_1$-$C_6$ alkyl.

18. The method of claim 17, each of $R^5$, $R^6$, $R^7$, $R^8$, and $R^9$ is independently halide, methyl, and OR, wherein R for each instance is independently hydrogen or $C_1$-$C_6$ alkyl.

19. The method of claim 17, wherein the injured neuron is an injured retinal ganglion cell or an injured dorsal root ganglion neuron.

* * * * *